United States Patent
Corneliusson et al.

(10) Patent No.: US 8,672,912 B2
(45) Date of Patent: Mar. 18, 2014

(54) ABSORBENT ARTICLE WITH IMPROVED FIT

(75) Inventors: Helena Corneliusson, Bohus (SE); Rozalia Bitis, Kungsbacka (SE); Ingrid Stjernholm, Lerum (SE)

(73) Assignee: SCA Hygiene Products AB, Gothenburg (SE)

( * ) Notice: Subject to any disclaimer, the term of this patent is extended or adjusted under 35 U.S.C. 154(b) by 516 days.

(21) Appl. No.: 12/597,824

(22) PCT Filed: May 21, 2007

(86) PCT No.: PCT/SE2007/050340
§ 371 (c)(1),
(2), (4) Date: Oct. 27, 2009

(87) PCT Pub. No.: WO2008/143560
PCT Pub. Date: Nov. 27, 2008

(65) Prior Publication Data
US 2010/0137823 A1 Jun. 3, 2010

(51) Int. Cl.
*A61F 13/15* (2006.01)
*A61F 13/20* (2006.01)

(52) U.S. Cl.
USPC ............ 604/385.24; 604/385.01; 604/385.25; 604/385.26; 604/385.27; 604/385.28; 604/385.29

(58) Field of Classification Search
USPC .......... 604/385.24, 29–30, 389–392, 385.01, 604/391
See application file for complete search history.

(56) References Cited

U.S. PATENT DOCUMENTS

| | | |
|---|---|---|
| 4,366,814 A | 1/1983 | Riedel |
| 5,226,992 A | 7/1993 | Morman |
| 5,376,430 A | 12/1994 | Swenson et al. |

(Continued)

FOREIGN PATENT DOCUMENTS

| | | |
|---|---|---|
| EP | 0 641 552 A1 | 3/1995 |
| EP | 0 646 062 A1 | 4/1995 |

(Continued)

OTHER PUBLICATIONS

International Search Report of Application No. PCT/SE2007/050340 dated Feb. 5, 2008.

(Continued)

*Primary Examiner* — Jackie Ho
*Assistant Examiner* — Aundria Hairell
(74) *Attorney, Agent, or Firm* — Buchanan Ingersoll & Rooney PC

(57) ABSTRACT

An absorbent article includes a chassis extending about a longitudinal axis and having a topsheet, a backsheet and an absorbent structure disposed between the topsheet and the backsheet. The chassis has a first transverse axis dividing the absorbent structure into a front body panel terminating in a front waist region and a rear body panel terminating in a rear waist region. The rear waist region has a first elastic region. The chassis is delimited by opposed longitudinal edges and opposed transverse edges. In the rear waist region, the absorbent structure terminates at a first distance from the transverse edge and the first elastic region extends substantially parallel to the transverse edge and spaced therefrom by a second distance and spaced from the absorbent structure by a third distance. The third distance is greater than said second distance or substantially equal thereto.

23 Claims, 9 Drawing Sheets

(56) References Cited

U.S. PATENT DOCUMENTS

| | | | |
|---|---|---|---|
| 5,669,897 A | 9/1997 | Labon et al. | |
| 5,749,866 A | 5/1998 | Roe et al. | |
| 5,885,268 A | 3/1999 | Bien et al. | |
| 5,904,675 A | 5/1999 | Laux et al. | |
| 6,423,048 B1 * | 7/2002 | Suzuki et al. | 604/385.28 |
| 6,476,289 B1 | 11/2002 | Buell et al. | |
| 6,585,713 B1 | 7/2003 | LeMahieu et al. | |
| 2003/0109843 A1 | 6/2003 | Gibbs | |
| 2004/0102745 A1 * | 5/2004 | Linker et al. | 604/356 |
| 2004/0116888 A1 | 6/2004 | Dorschner | |
| 2004/0133181 A1 | 7/2004 | Ishiguro et al. | |
| 2004/0236300 A1 * | 11/2004 | Gibbs et al. | 604/385.24 |
| 2004/0260261 A1 | 12/2004 | Yoshida et al. | |
| 2005/0027279 A1 | 2/2005 | Minato et al. | |
| 2005/0038400 A1 | 2/2005 | Poruthoor | |
| 2005/0131373 A1 | 6/2005 | Wright et al. | |
| 2005/0215962 A1 * | 9/2005 | Litvay et al. | 604/358 |
| 2005/0215963 A1 | 9/2005 | Autran et al. | |
| 2005/0256480 A1 * | 11/2005 | La Von et al. | 604/385.01 |
| 2006/0004339 A1 | 1/2006 | Lord et al. | |

FOREIGN PATENT DOCUMENTS

| | | |
|---|---|---|
| EP | 0 913 137 | 5/1999 |
| EP | 1 179 331 A2 | 2/2002 |
| EP | 1 384 457 A2 | 1/2004 |
| GB | 2 244 422 A | 12/1991 |
| GB | 2 284 538 | 6/1995 |
| GB | 2 292 067 A | 2/1996 |
| GB | 2 389 665 A | 12/2003 |
| RU | 2 179 008 | 2/2002 |
| WO | WO 94/00292 A1 | 1/1994 |
| WO | WO 98/29251 A1 | 7/1998 |
| WO | WO 00/37005 A2 | 6/2000 |
| WO | WO 03/000165 A1 | 1/2003 |
| WO | WO 03/030775 A2 | 4/2003 |
| WO | WO 03/047488 A1 | 6/2003 |
| WO | WO 2006/065175 A1 | 6/2006 |
| WO | WO 2006/074481 A2 | 7/2006 |
| WO | WO 2007/071267 A1 | 6/2007 |
| WO | WO 2008/039112 A1 | 4/2008 |

OTHER PUBLICATIONS

Office Action (Decision on Grant) dated Nov. 29, 2010, issued in the corresponding Russian Patent Application No. 2009147283, and an English Translation thereof.

Supplementary European Search Report dated Mar. 16, 2012 issued in the corresponding European Patent Application No. 07748501.9-2124/2157958.

* cited by examiner

ABSORBENT ARTICLE WITH IMPROVED FIT

TECHNICAL FIELD

The present invention relates to an absorbent article, such as a disposable diaper or an incontinence guard, for an adult or a child.

BACKGROUND OF THE INVENTION

Disposable diapers conventionally include a chassis having liquid permeable topsheet, a liquid impermeable backsheet and an absorbent structure sandwiched between the topsheet and backsheet. The chassis has a front body panel which, in use, extends over the stomach and front hip area of the user, and a rear body panel which, in use, extends over the back and the rear hip area of the user. Each of the body panels has a waist portion such that, when the diaper is fastened around the waist of the user, the waist portions provide a continuous encirclement of the user. In order to fasten the diaper around the waist of a user, a fastening system comprising fastening tabs is commonly employed. Fastening tabs may be provided on side panels which extend from lateral side edges of the diaper chassis.

As a user of a diaper moves about (i.e. eats, breathes, sneezes, crawls, walks, jumps, etc.), the circumference of the user's waist expands and contracts, which consequently results in the waist portions of the diaper being strained and relaxed. Repeated or exaggerated expansion and contraction of the waist portions can lead to permanent deformation of the waist portions, resulting in a slackening on the diaper around the waist. Particularly for active toddlers wearing diapers which already contain an insult, this often results in the diaper slipping down, thereby increasing the risk for leakage.

To reduce the risk of leakage when worn, a diaper should be provided with form-fitting properties at least in some areas. The form-fitting properties also contribute to an improved appearance of the diaper when worn by the user. Typically, one or both waist portions may contain an elastic waistband. Furthermore, the side panels on which the fastening tabs are provided may display elastic properties. However, elastic material is generally more expensive than non-elastic material and in many cases has poor breathability.

Even though conventional diapers may exhibit some form-fitting properties, the resistance to leakage is nevertheless increased if the diaper is not correctly fastened around the waist of a user.

When a user purchases an absorbent article it is not possible for him/her to predict how well the absorbent article stay in place when in use since test methods according to the prior art do not provide such information. Only test specimens cut from the fabrics that constitute an absorbent article are tested in known test methods. A disadvantage with testing only a test specimen of fabric is that an absorbent article usually comprises several different parts comprising various materials, which are used to fasten the absorbent article around a user's waist, such as adhesive tape, elasticated sections, elastic panels and other attached or integrated elements. It is therefore difficult to determine the net elastic and tensile properties of all of said parts/materials from an analysis of each part/material separately. Furthermore, the weight of an absorbent article and its contents are not taken into account in the tests carried out on a test specimen, even though the weight of an absorbent article and its contents will influence how well the absorbent article stays in place on a user.

SUMMARY OF THE INVENTION

It is an object of the present invention to provide an elasticized absorbent article, such as a disposable diaper or an incontinence guard, in which the elastic regions of the absorbent article are arranged so as to reduce the risk of incorrect fastening of the absorbent article around the waist of the user and so that the absorbent article will have an improved and comfortable fit, attractive appearance and the capability to stay in place during normal use.

This object is achieved by an absorbent article comprising a chassis extending about a longitudinal axis, the chassis including a topsheet, a backsheet and an absorbent structure disposed between the topsheet and the backsheet. The chassis has a first transverse axis dividing the absorbent structure into a front body panel terminating in a front waist region and a rear body panel terminating in a rear waist region that has a first elastic region. The chassis is delimited by opposed longitudinal edges and opposed transverse edges. A pair of opposed rear side panels is attached to the chassis at the rear waist region of the rear body panel. Each rear side panel extends outwardly from the respective longitudinal edge of the chassis. At least one of the rear side panels has a second elastic region. The absorbent article also comprises a fastening system, for example a mechanical fastening system, especially a hook-and-loop fastening means, for fastening the absorbent article around the waist of a user. The fastening system comprises first fastening means arranged on the pair of opposed rear side panels and complementary second fastening means arranged on the front body panel.

In the rear waist region, the absorbent structure terminates at a first distance from the transverse edge. The first elastic region extends substantially parallel to the transverse edge and spaced therefrom by a second distance and spaced from the absorbent structure by a third distance. The first elastic region terminates short of a first longitudinal edge by a fourth distance, wherein the third distance is greater than the second distance or substantially equal thereto. The first fastening system comprises a first fastening member on each opposed rear side panel, the first fastening members being positioned on a second transverse axis extending substantially parallel to the first transverse axis, with the second transverse axis passing between the absorbent structure and the first elastic region. The synergistic effect that occurs between the first and second elastic regions when the absorbent article is in use makes the absorbent article not only comfortable to wear and easy to fasten and handle, but also provides a good fit and ensures that the absorbent article stays reliably in place during use even if its user is very active.

The first and second elastic regions are arranged to be capable of being elongated in a substantially transverse direction of the absorbent article, whereby the expressions "elastic" and "inelastic" as used in this document are defined using the elasticity test described below.

Elasticity Test

The elasticity test measures how an elastic material behaves during repeated load and unload cycles. The test sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The test sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:
Crosshead speed: 500 mm/min
Clamp distance: 50 mm
Preload: 0.05 N The test sample is placed in the clamps according to the marks and it is made sure that the test sample is centred and fastened perpendicularly in the clamps. The tensile tester is started and three cycles between 0 and the predetermined elongation, equal to the highest defined first load, are performed. Before the last cycle, the test sample is relaxed for one minute, then the permanent elongation is measured by stretching the test sample until a force of 0.1 N is detected and the elongation is read.

An elastic material is defined as a material having a permanent elongation after relaxation of less than 10% after the material has been subjected to an elongation of 30% in the aforementioned elasticity test. An elongation of 30% means an elongation to a length that is 30% longer than the initial length of the sample. An inelastic material has a permanent elongation after relaxation of more than 10% after having been subjected to an elongation of 30%.

As regards the fastening system of the absorbent article, the external surface of the front panel may, for example, constitute or comprise a reception surface for the first fastening means, i.e. the backsheet of the front panel may be arranged to function as a reception surface for the first fastening means, or a panel of material that is arranged to function as a reception surface for the first fastening means may be attached to the external surface of the front panel. In cases where the first fastening means is a hook fastener a non-woven material may be used as the complementary second fastening means. In cases where the first fastening means is an adhesive tape tab, a plastic film may be suitable as reception material as well as non-woven material. Further examples of mechanical fastening systems are button and holes or button loops, snap fasteners and the like.

"Hook-and-loop fastening means" refers to a fastening system having a "hook" portion (first fastening means and a "loop" portion (complementary secondary fastening means) and which are re-fasteable. The term "hook" as used herein refers to any element capable of engaging another element, the so called "loop" portion. The term "hook" is not limited to only "hooks" in its normal sense, but rather encompasses any form of engaging elements, whether uni-directional or bi-directional. The term "loop" is likewise not limited to "loops" in its normal sense, but also encompasses any structure capable of engaging with a "hook" fastener. Examples of "loop" materials are fibrous structures, like non-woven materials. Hook-and-loop fasteners are for example available from Velcro, USA. Alternatively the first fastening means is an adhesive fastening means such as an adhesive tape tab wherein at least part of the external surface of a front panel may be of a material to which the tape can adhere (complementary secondary fastening means).

According to an embodiment of the invention the distance of the absorbent structure from the transverse edge of the back panel (the first distance) is between 40-140 mm, preferably between 80-130 mm and most preferably between 95-115 mm. The distance of the first elastic region from the transverse edge of the back panel (the second distance) is between 5-40 mm and preferably between 10-30 mm. The distance of first elastic region from the absorbent structure (the third distance) is between 10-60 mm, preferably between 10-50 mm and most preferably between 15-40 mm. The distance of the first elastic region from each longitudinal edge of the back panel (the fourth distance) is between 30-120 mm, preferably between 40-100 mm and most preferably between 50-90 mm.

According to an embodiment of the invention the first and second elastic regions are tailored such that when tested on Cyclic Waist Expansion Test apparatus, as described below, the absorbent article does not slip down more than 15 mm from its initial position on the Cyclic Waist Expansion Test apparatus during at least fifteen expansion/contraction cycles of the Cyclic Waist Expansion Test and within 5-10 seconds after being subjected to at least ten expansion/contraction cycles of the Cyclic Waist Expansion Test.

According to another embodiment of the invention the absorbent article does not slip down more than 10 mm and most preferably not more than 7 mm from its initial position on the Cyclic Waist Expansion Test apparatus described herein. A graded scale of how well an absorbent article stays on the Cyclic Waist Expansion Test apparatus can therefore be defined by how much the absorbent article slips down from its initial position during and after being subjected to at least ten expansion/contraction cycles of the Cyclic Waist Expansion Test.

According to another embodiment of the invention the first and second elastic regions are tailored such that when tested using a tensile testing machine using a force of 7N, as described herein, the ratio of the extension of the first elastic region to the extension of the second elastic region is in the range 35:60 to 50:60, such as 44:56 for example.

According to another embodiment of the invention the first elastic region terminates short of each opposed longitudinal edge by the fourth distance, i.e. it is centred between the opposed longitudinal edges of the chassis.

According to a further embodiment of the invention the first elastic region is constituted by an elastic film. The elastic film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials.

According to an embodiment of the invention the second elastic region constitutes an elastic laminate comprising at least one elastic film layer and at least one non-woven layer, in which the layers have been ultrasonically bonded, adhesively bonded or extrusion bonded, or bonded using a combination of the bonding methods. For such elastic laminates it is preferred that the first and second layers of fibrous material are chosen so that they, in combination with the intermediate elastic film layer, provide a soft and cloth-like feel to the laminate. Examples of suitable materials are carded webs and spun-bonded materials. Examples of suitable polymers used in the fibrous materials are polyethylene, polyesters, polypropylene and other polyolefin homo-polymers and copolymers. Natural fibres, for example cotton, may also be used as long as they provide the required properties. A mixture of polymers can contribute to a higher flexibility of the non-woven layer.

According to an embodiment of the invention, when the layers of the elastic laminate have been ultrasonically bonded, the male side of the bonding points are arranged to be located towards the body of the user of the absorbent article when said absorbent article is in use. The male side of said bonding points is the non-woven surface comprising projections, such as projecting fibres, and the female side of said bonding points is the surface comprising depressions.

The second elastic region may comprise a stretch activated laminate, activated by hot stretching for example, and known in the art. The elastic laminate may be a laminate between two or more non-woven layers, two or more film layers or a combination of film and non-woven layers. One group of elastic laminates are so called "stretch-bonded" laminates, in which the elastic layer is stretched in at least one direction before laminating it with one or more inelastic layers. After the tension is removed from the elastic layer it can freely retract to its un-tensioned state, and the inelastic layer(s) laminated thereto become gathered, giving a three-dimensional puckering. Alternatively, the second elastic region may comprise one or more elastic strips or threads contractably affixed between web materials, which may be inelastic.

Another group of elastic laminates are so called "neck bonded" laminates, which refer to laminates in which an elastic material is bonded to a non-elastic material while the non-elastic member is extended under conditions reducing its width or "necked". "Neck bonded laminate" refers to a composite material having at least two layers in which one layer is a necked, non-elastic layer and the other layer is an elastic layer. The layers are joined together when the non-elastic layer is in an extended condition.

A further group of elastic laminates are disclosed in for example WO 03/047488, in which inelastic non-woven layers are laminated to an elastic film layer, and the laminate is stretched above the point of failure of the non-woven materials, so that the inelastic layers break. Inelastic non-woven layers may also be laminated to an un-stretched elastic film layer. The elasticity of the laminate is then activated by mechanical stretching.

Examples of elastic laminates are described in EP-B-0 646 062, WO 98/29251, WO 03/000165 and U.S. Pat. No. 5,226, 992. Examples of commercially available elastic laminates are Fabriflex™ 306 from Tredegar and PK 6358 from Nordenia.

According to another embodiment of the invention the second elastic region is constituted by substantially the entire at least one rear side panel. The second elastic region may however be attached by adhesive, thermo-bonding, ultrasonic or laser welding to a substantially inelastic part of the at least one rear side panel, resulting in an overlap of elastic and substantially inelastic material, whereby the length of said overlap as measured in the transverse direction may be up to 15 mm. All of the dimensions of elastic regions along the transverse direction of the absorbent article which are given in this document refer to the active elastic length i.e. the length of the elastic material which can be elongated on application of an elongating force in the transverse direction of the absorbent article and retracted when releasing the force, whereby the expression "elastic material" is as defined according to the aforementioned elasticity test.

According to an embodiment of the invention the ratio of the distance of the first elastic region from the transverse edge of the rear body panel to the distance of the absorbent structure to the transverse edge of the rear body panel is between 1:2 and 1:9, preferably between 1:3 and 1:5, i.e. the ratio of the second distance to the first distance is between 1:2 and 1:9, preferably between 1:3 and 1:5.

According to another embodiment of the invention the ratio of the third distance to the first distance is between 1:3 and 1:9, preferably between 1:4 to 1:45. According to an alternative embodiment of the invention the ratio of the fourth distance to the width of the rear body panel in the rear waist region is between 1:20 to 1:45, preferably between 1:30 to 1.40. The width of the rear body panel is measured in the transverse direction of the absorbent article in between the peripheral longitudinal edges of the chassis to which the rear side panels are attached.

According to an embodiment of the invention the first elastic region extends along 25-55% of the width of the rear body panel in the rear waist region in the transverse direction (T) of the absorbent article, preferably along 30-45% of the width of the rear body panel in the transverse direction (T) of the absorbent article, as measured in the initial non-elongated state of the rear body panel.

According to another embodiment of the invention the first elastic region extends 1 to 5 cm in the longitudinal direction of the absorbent article, preferably 2-3 cm in the longitudinal direction of the absorbent article.

According to an embodiment of the invention the absorbent structure in the rear body panel is thinner than the absorbent structure in the front body panel, namely up to 50% thinner, preferably up to 25% thinner. According to an embodiment of the invention the absorbent structure is thinnest in the vicinity of the rear waist region and has for example a thickness of 3-5 mm in the vicinity of the rear waist region (measured to an accuracy of ±0.03 mm using a thickness gauge with a foot having an area of 50 $cm^2$ and using a load pressure of 0.5 kPa).

According to an embodiment of the invention the absorbent article comprises material, such as topsheet material and breathable backsheet material, which constitutes at least one breathable zone located in between a longitudinal edge of the chassis and a longitudinally extending edge of the first elastic region, i.e. an edge that extends in the longitudinal direction of the absorbent article. The expression "breathable" means that said zone or material will allow water vapour to pass through it. The at least one breathable zone may for example comprise a soft non-woven having a fine dernier or a microporous or monolithic plastic film, which is intended to be in direct contact with the skin of a user of the absorbent article. A suitable non-woven material can be a spun-bonded material of polypropylene or polyethylene fibres. The at least one breathable zone provides a chimney-like effect, which promotes air circulation within the absorbent article and consequently decreases the temperature inside the absorbent article during its use as compared to a non-breathable material.

According to another embodiment of the invention the absorbent article comprises a pair of opposed front side panels, comprising a nonwoven material for example, attached to the front body panel. The front side panels have a surface roughness where the vertical distance between a surface containing 5% of the material constituting a front side panel and a surface containing 95% of the material constituting a front side panel (an SDC 5-95% value) is 46 to 48 µm as measured using a stripe light projection (SLP) method (as described below and schematically illustrated in FIG. 14) and using MikroCAD optical 3D measuring device from GFMesstechnik from Göttingen, wherein the front side panel material sample is placed on a planar surface and covered with plate glass through which measurements are made at a surface developed ratio or surface magnification of 125-128%.

In the SLP method a stripe of light from a triangulation laser is swept across a sample of material. A camera is used to determine the distance of a point along the stripe from the camera, which varies depending on how far away the laser stripe strikes a surface of the sample. The point on the laser stripe, the camera and the laser emitter form a triangle. The length of one side of the triangle, the distance between the camera and the laser emitter is known. The angle of the laser emitter corner is also known. The angle of the camera corner can be determined by looking at the location of the laser dot in the camera's field of view. These three pieces of information fully determine the shape and size of the triangle and provide the location of the laser dot corner of the triangle.

The optical 3D measuring device MikroCAD is designed for the three-dimensional inspection of the surface profile and roughness of small samples and operates with a high measuring velocity and high precision. The contact-less measurement method implements digital fringe projection based on micro mirrors. The 3D profile of the sample may be acquired within a few seconds.

According to a further embodiment of the invention the first elastic region is located between the topsheet and the backsheet. If the first elastic region were to be placed outside the topsheet so that it were located adjacent to the skin of a user when the absorbent article were in use, it would create more friction against the skin of the user and thus make the absorbent article less comfortable to wear.

According to an embodiment of the invention each of the opposed longitudinal edges comprises a leg contour, i.e. a curved outline that is arranged to fit around the leg of a user, and that the absorbent article comprises leg elastic that is arranged to extend in a curved line that is substantially parallel to the leg contour when the chassis is fully extended. The leg elastic may comprise a plurality of elastic members, such as elastic threads that are contractably affixed between the topsheet and the backsheet of the absorbent article. The absorbent article may also be provided with so called barrier cuffs, in order to provide an improved security against leakage. These barrier cuffs may in some instances replace leg elastics.

According to an embodiment of the invention the chassis comprises at least one absorbent-structure-free channel that extends substantially in the longitudinal direction of the absorbent article to facilitate the absorbent article assuming a bowl-like shape when in use.

According to an embodiment of the invention the absorbent article is intended for a child, i.e. a baby or an infant, that weighs 4-25 kg for example. It should be noted that an absorbent article according to an embodiment of the invention is suitable for a child having a weight of 4-25 kg and that the absorbent article is not arranged to fit all children in that weight range.

According to another embodiment of the invention the absorbent article is arranged to be fastenable around the contoured plates of the Cyclic Waist Expansion Test apparatus, as described herein, in the manner described herein.

According to a further embodiment of the invention the absorbent article comprises elastic regions in the rear waist region only, i.e. the front waist region comprises no waist elastic.

It should be noted that the absorbent article according to any of the embodiments of the invention may be worn with the front waist region located at the front of the wearer and the rear waist region located at the back of the wearer. Alternatively, the absorbent article according to any of the embodiments of the invention may be worn with the front waist region located at the back of the wearer and the rear waist region located at the front of the wearer.

BRIEF DESCRIPTION OF THE DRAWINGS

The present invention will hereinafter be further explained by means of non-limiting examples with reference to the appended figures where.

It should be noted that the drawings have not been drawn to scale and that the dimensions of certain features have been exaggerated for the sake of clarity.

DETAILED DESCRIPTION OF EMBODIMENTS

Figure 1:
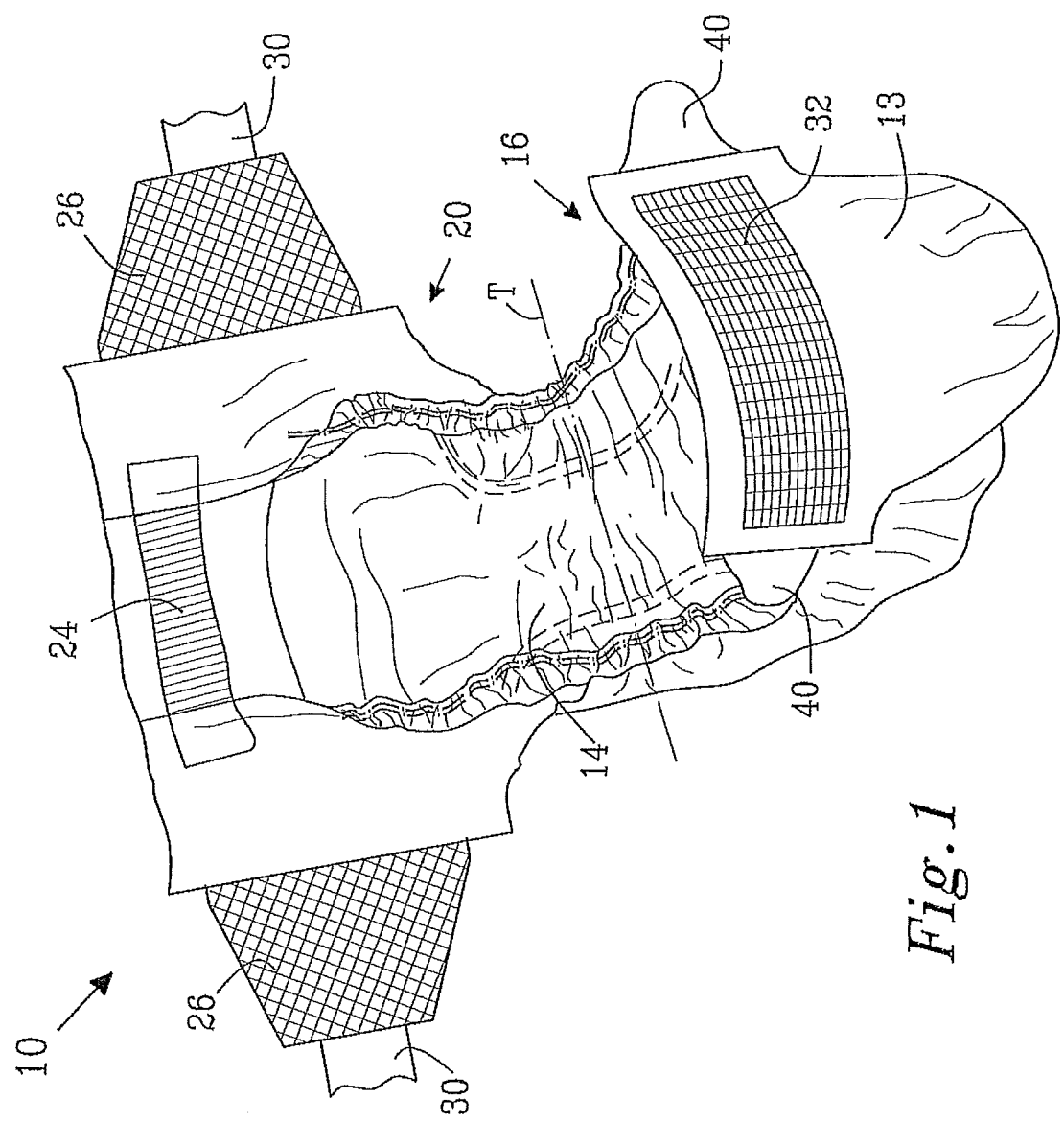
FIGS. 1 & 2 show an absorbent article according to an embodiment of the invention.
Figure 2:
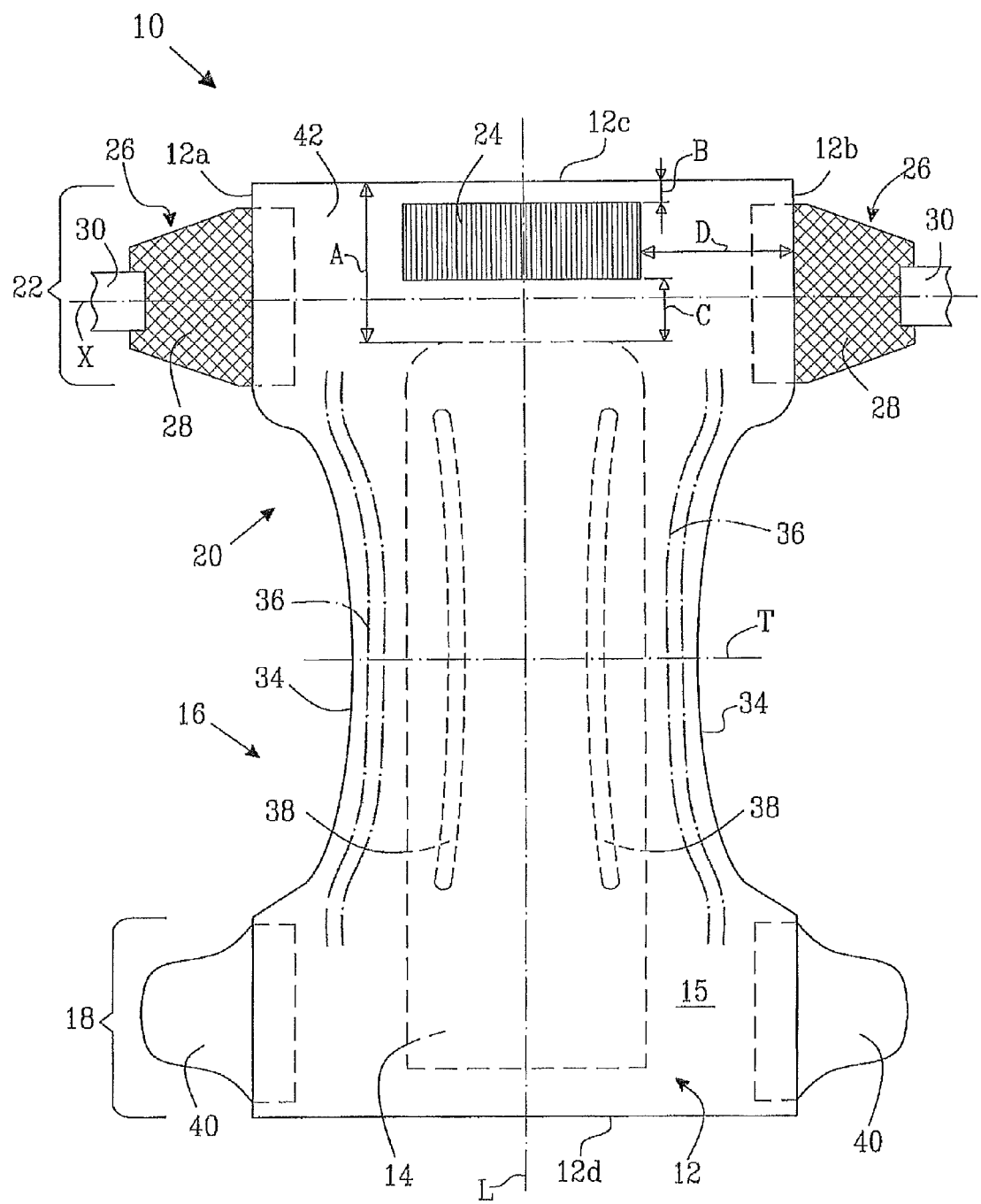

FIGS. 1 and 2 show an absorbent article 10, namely a disposable diaper that assumes a pant-like shape when fastened around the waist of a user. The absorbent article 10 comprises a chassis 12 extending about a longitudinal axis, L, said chassis including a topsheet 13, a backsheet 15 and an absorbent structure 14 disposed between said topsheet 13 and said backsheet 15. The chassis 12 has a first transverse axis, T, dividing the absorbent structure 14 into a front body panel 16 terminating in a front waist region 18 and a rear body panel 20 terminating in a rear waist region 22 that has a first elastic region 24, constituted by an elastic film for example, located between the topsheet 13 and the backsheet 15 of the chassis 12. The first elastic region 24 may be contractably attached between the topsheet 13 and backsheet 15 or it may be contractably attached to the inside surface of the topsheet 13 or the inside surface of the backsheet 15, whereby the "inside surface is the surface facing the absorbent structure 14.

The chassis 12 is delimited by opposed longitudinal edges 12a and 12b and opposed transverse edges 12c and 12d. A pair of opposed rear side panels is attached to the chassis 12 at the rear waist region 22 of the rear body panel 20. Each rear side panel 26 extends outwardly from the respective longitudinal edge 12a, 12b of the chassis 12. At least one of the rear side panels 26 has a second elastic region 28. The absorbent article 10 also comprises a fastening system for fastening the absorbent article 10 around the waist of a user. The fastening system comprises first fastening means 30 arranged on the pair of opposed rear side panels 26 and complementary second fastening means 32 arranged on the front body panel 16.

The illustrated absorbent article 10 also comprises leg contours 34 and leg elastic 36 that is arranged to extend in a curved line that is substantially parallel to the leg contour when the chassis 12 is fully extended. The illustrated absorbent article 10 also comprises at least one absorbent-structure-free channel 38 that extends substantially in the longitudinal direction L of the absorbent article 10 and a pair of opposed front side panels 40 attached to the front body panel 16. Furthermore, the illustrated absorbent article 10 comprises at least one breathable zone 42, which is located in between a longitudinal edge 12a, 12b of the chassis 12 and a longitudinal edge of the first elastic region 24.

In the rear waist region 22, the absorbent structure 14 terminates at a first distance A from the transverse edge 12c. The first elastic region 24 extends substantially parallel to the transverse edge 12c and is spaced therefrom by a second distance B and spaced from the absorbent structure 14 by a third distance C. The first elastic region 24 terminates short of a first longitudinal edge 12b by a fourth distance D, wherein the third distance C is greater than the second distance B or substantially equal thereto. In the illustrated embodiment the first elastic region 24 terminates short of each opposed longitudinal edge 12a and 12b by the fourth distance D, i.e. the first elastic region 24 is centred between the opposed longitudinal edges 12a and 12b of the chassis 12.

The first fastening system comprises a first fastening member 30 on each opposed rear side panel 26, the first fastening members 30 being positioned on a second transverse axis X extending substantially parallel to the first transverse axis T, with the second transverse axis X passing between the absorbent structure 14 and the first elastic region 24.

The absorbent structure 14 can be of any conventional kind. Examples of commonly occurring absorbent materials are cellulosic fluff pulp, tissue layers, highly absorbent polymers (so called super-absorbents), absorbent foam materials, absorbent non-woven materials or the like. It is common to combine cellulosic fluff pulp with super-absorbent polymers in an absorbent structure. Super-absorbent polymers are water-swellable, water-insoluble organic or inorganic materials capable of absorbing at least about 10 times their own weight of an aqueous solution containing 0.9 weight percent of sodium chloride. Organic materials suitable for use as super-absorbent materials can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred super-absorbent materials are further surface cross-linked so that the outer surface or shell of the super-absorbent particle, fibre, flake, sphere, etc. possesses a higher crosslink density than the inner portion of the super-absorbent.

A high liquid storage capacity is provided by the use of large amounts of super-absorbent material. For an absorbent structure comprising a matrix of hydrophilic fibres, such as cellulosic fibres, and super-absorbent material, the proportion of super-absorbent material is preferably between 10 and 90% by weight, more preferably between 30 and 70% by weight.

It is conventional for absorbent articles to have absorbent structures comprising layers of different properties with respect to liquid receiving capacity, liquid distribution capacity and storage capacity. The thin absorbent structures, which are common in, for example, disposable diapers and incontinence guards, often comprise a compressed, mixed or layered structure of cellulosic fluff pulp and super-absorbent polymers. The size and absorbent capacity of the absorbent structure may be varied to suit different uses, such as infants or adult incontinent persons.

The absorbent structure may further include an acquisition distribution layer placed on top of the primary absorbent body, which is adapted to quickly receive and temporarily store discharged liquid before it is absorbed by the primary absorbent structure. Such acquisition distribution layers are well known in the art and may be composed of porous fibrous wadding or foam materials.

According to an embodiment of the invention the absorbent structure 14 in the rear body panel 20 is thinner than the absorbent structure in the front body panel 20, namely up to 50% thinner, preferably up to 25% thinner. The absorbent structure 14 illustrated in FIG. 2 has a rounded end in the vicinity of the rear waist region 22 and is arranged to have a gradually decreasing thickness in the longitudinal direction L of the absorbent article starting from the point at which the longitudinal axis L cross the first transverse axis T in FIG. 2 outwardly to the rounded end. The decreased thickness of the rounded end of the absorbent structure 14 allows the rounded end to gather around the waist of the user's body and thus provide an improved fit when the absorbent article 10 is in use and it also makes the absorbent article 10 lighter.

Figure 3:
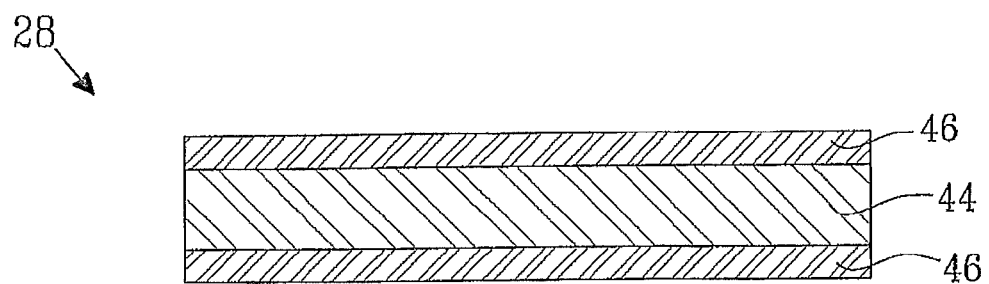
FIG. 3 shows a cross section of an elastic laminate according to an embodiment of the invention.

FIG. 3 shows schematically an elastic laminate that is suitable for use as the second elastic region 28 of the rear side panel 26. The elastic laminate comprises an elastic film 44 comprising a styrene butadiene copolymer, sandwiched between two necked non-woven layers 46, such as polypropylene or polyethylene non-woven layers, whereby the layers of said elastic laminate are ultrasonically bonded together. According to an embodiment of the invention at least one rear side panel of the absorbent article comprises at least one such elastic laminate. According to another embodiment of the invention substantially an entire rear side panel 26 or both rear side panels 26 is/are constituted by such an elastic laminate.

Tensile Test Procedure

Figure 4:
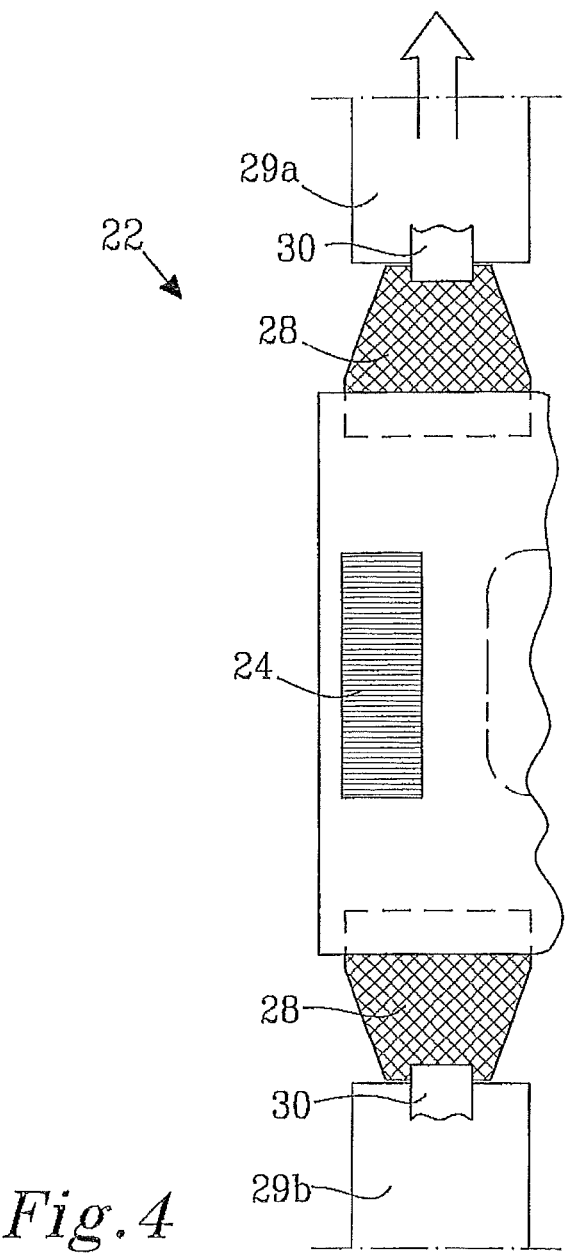
FIG. 4 shows a rear waist region according to an embodiment of the invention prior to testing using a tensile testing machine.

FIG. 4 schematically represents the test used to determine the interaction between the first (24) and the second elastic regions (28) in an absorbent article 10 as illustrated in FIG. 1. The rear waist region 22 of an absorbent article 10 was tested using a tensile testing machine (Lloyd LRX) using a force of 7 N (cell 50 N, test speed 300 mm/min, preload force of 0.1 N, clamps 50 mm, ruler accuracy ±0.3 mm). Seven Newtons is considered to be a suitable force when applying the product on a user. The tests were carried out in a climatised room at a temperature of 23±1° C., relative humidity of 50±5% whereby the samples to be tested were climatised in the room for at least two hours before the tests.

The absorbent article 10 was firstly cut to obtain a rectangular test sample comprising substantially only the rear waist region 22. The first fastening means 30 of the rear waist section 22 were clamped in the upper and lower clamps 29a and 29b of a tensile testing machine respectively, whereby the upper clamp 29a was arranged to move vertically and the lower clamp 29b was arranged to remain stationary during the test. The test sample was centred and fastened perpendicularly in the clamps 29a, 29b. The edge of each clamp 29a and 29b was positioned at the outermost edge of the second elastic regions 28 as shown in FIG. 4. The length of the first elastic region 24 and the second elastic region(s) 28 in their relaxed state was measured with a ruler. After the test sample had been fastened between the clamps 29a and 29b the test sample was elongated to a preload force of 0.1 N. The upper clamp 29a was then moved vertically upwards at a constant speed of 300 mm/min until the tensile force was 7 N. The length of the first elastic region 24 and the second elastic region(s) 28 was measured using a ruler.

The following equations were used to determine the % elongation of the first and second elastic regions:

Total initial length of first elastic region 24 and second elastic regions 28:

$$L0 = L0_{1st} + (2 \times L0_{2nd})$$

where $L0$ is the total length of elastic material when the rear waist region 22 is in a non-elongated state, $L0_{1st}$ is the average length of the first elastic region 24 when the rear waist region 22 is in a non-elongated state, and $L_{2ndt}$ is the average length of the second elastic regions 28 when the rear waist region 22 is in a non-elongated state.

Total length of first elastic region 24 and second elastic regions 28 at 7N:

$$L_{7N} = L_{1st} + (2 \times L_{2nd})$$

$L_{7N}$ is the total length of elastic material when the rear waist region 22 is subjected to a force of 7N, $L_{1st}$ is the average length of the first elastic region 24 when the rear waist region 22 is subjected to a force of 7N, and $L_{2ndt}$ is the average length of the second elastic regions 28 when the rear waist region 22 is subjected to a force of 7N.

$$\% \text{ elongation of the first elastic region, } E_{1st} = \frac{L_{1st} - L0_{1st}}{L_{7N} - L0} * 100$$

$$\% \text{ elongation of the second elastic region, } E_{2nd} = \frac{1}{2}(100 - E_{1st})$$

The tests were carried out on absorbent articles intended for infants. The topsheet 13 of the tested absorbent articles according to an embodiment of the invention was constituted by a thermally bonded spunbound nonwoven, available from BBA Nonwovens of Sweden (supplier code 4 WHO5-01 017H) and comprising a minimum of 97% polypropylene, a maximum of 2% polyethylene, 0.3-1% $TiO_2$ and a maximum of 0.6% surfactant (BHQ). The backsheet 15 was constituted by a glue-laminated nonwoven/microporous film laminate available from Nuova Pansac (supplier code Mira air 37B32). The first elastic region was constituted by an elastic film available from Nordenia (supplier code KC 6425.000), which comprised a cast film, coextruded in three layers; a middle layer of SBS (42 μm thick) and outer layers of polyolefin (2×4 μm). The elastic film had a length of 90 mm in its relaxed state before it was attached to the absorbent article, it was then elongated to 140 mm and attached to the absorbent article whereby the outermost 5 to 7 mm at each end of the elastic film were not elongated, i.e. only the central portion of the elastic film had been elongated prior to the elastic film's attachment to the absorbent article. The rear side panels which constituted the second elastic regions were constituted by an ultrasonically bonded elastic laminate available from Tredegar Film Products (Supplier code Fabriflex 306) which comprises a soft PP/PE nonwoven and a high force elastic film, whereby the non-woven side of the laminate constitutes the male side of the laminate that is worn against a user's skin.

The tested absorbent articles were tailored as follows: the distance of the absorbent structure from the transverse edge of the back panel (the first distance) was 105 mm. The distance of the first elastic region from the transverse edge of the back panel (the second distance) was 20 mm. The distance of first elastic region from the absorbent structure (the third distance) was 25 mm. The distance of the first elastic region from each longitudinal edge of the back panel (the fourth distance) was 75 mm. The first elastic region 24 had an extension of 135 mm in the first transverse direction T of the absorbent article and an extension of 25 mm in the longitudinal direction L of the absorbent article.

In their relaxed state, the rear side panels 30 had an extension of 55 mm in the first transverse direction T of the absorbent article and an extension of 83 mm in the longitudinal direction L of the absorbent article.

It was found that the ratio of the extension of the first elastic region to the extension of the second elastic region of the absorbent article according to an embodiment of the invention was 44:56 whereas the following commercially available products had the following ratio: Huggies Super Flex 84:16, Huggies Natural Fit 83/17 and Unicharm Moneyman 53:47.

Cyclic Waist Expansion Test

Figure 5:
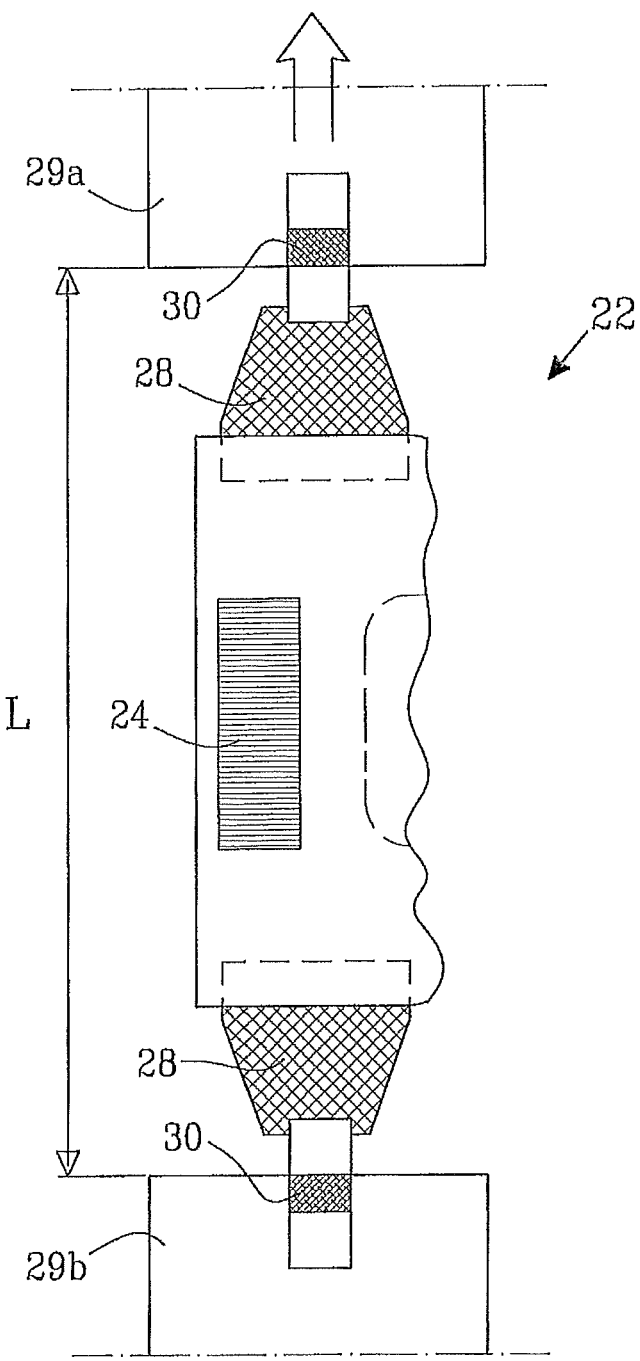
FIG. 5 shows a rear waist region according to an embodiment of the invention being tested on a tensile testing machine to determine a length, $L_{7N}$ FIGS. 6-12 schematically show the Cyclic Waist Expansion Test Apparatus according to an embodiment of the invention.

FIG. 5 shows a test sample constituted substantially of only the rear waist region 22 of an absorbent article according to an embodiment of the invention being tested on a tensile testing machine to determine a length, $L_{7N}$ prior to testing absorbent articles of the same size and type on the Cyclic Waist Expansion Test Apparatus. The test sample 22 is clamped between the upper and lower clamps 29a and 29b of a tensile testing machine as shown in FIG. 5. The edge of each clamp 29a and 29b is namely positioned at the innermost edge of the first fastening means 30. The test sample 22 is elongated to a preload force of 0.1N. The upper clamp 29a is then moved vertically upwards at a constant speed of 300 mm/min until the tensile force is 7 N. The length, $L_{7N}$, is then measured. This test procedure is similar to the test procedure used in the tensile test described above. The only difference is the position of the clamps.

Figure 6:
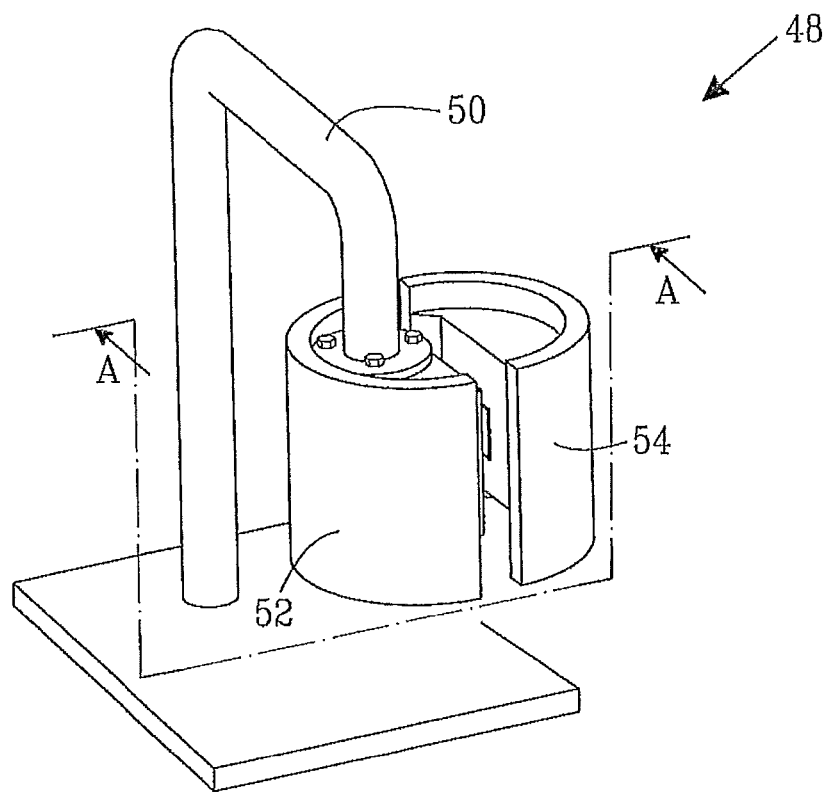

FIG. 6 schematically shows a perspective view of the Cyclic Waist Expansion Test Apparatus 48 according to an embodiment of the invention. The test equipment 48 comprises a stand 50 that supports two contoured plates 52, 54 which are formed to mechanically simulate a human user's waist. The contoured plates 52, 54 are supported by the stand 48 in such a way that the stand 48 does not hinder any part of an absorbent article from being wrapped around the contoured plates 52, 54. An absorbent article 10 is wrapped around the contoured plates 52, 58 and the rear side panels 26 are fastened to the external surface of the front panel 16 of the absorbent article 10 in a stretched position, as will be described below.

Figure 7:
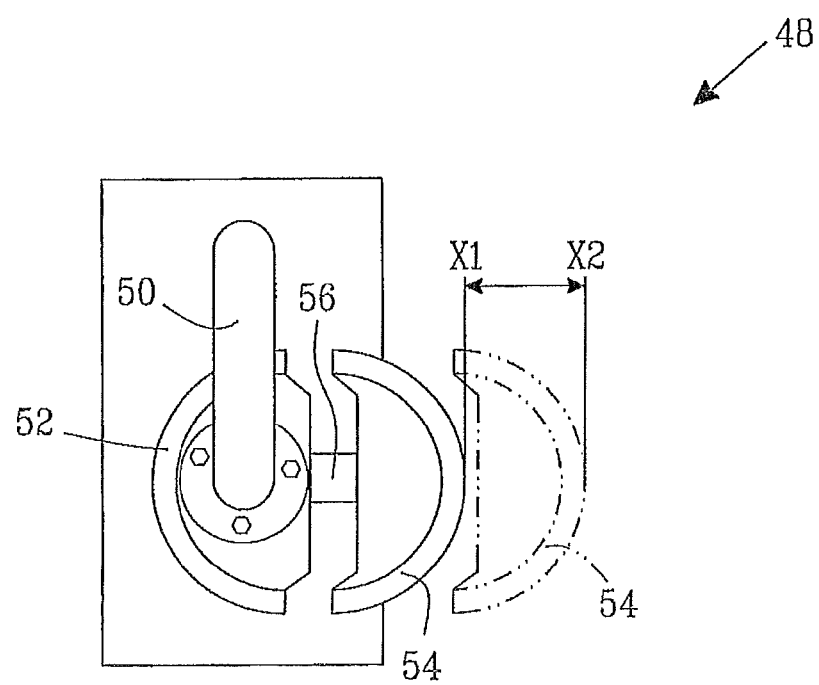

FIG. 7 shows the Cyclic Waist Expansion Test Apparatus 48 from above. Once absorbent article has been fastened around the contoured plates 52, 54, actuating means 56 force the second contoured plate 54 away from the first mechanical member 52 from its initial position X1 to an outer position X2 (using an air pressure of 4 bar) and then back to its initial position X1 (which constitutes one expansion/contraction cycle) a number of times so as to simulate the expansion and contraction of a user's waist as he/she moves. The apparatus' mechanical motion speed (V) is set to 15 cycles per 22 seconds and there is no pause between cycles.

Figure 8:
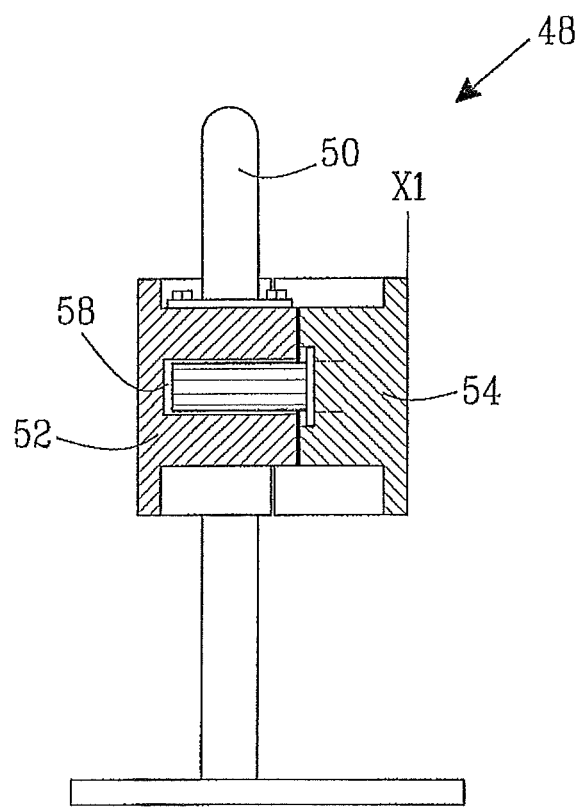

FIGS. 7 and 8 show cross-sections of the Cyclic Waist Expansion Test Apparatus 48 (as viewed in the vertical plane A-A shown in FIG. 4). The contoured plates 52, 54 are shown in their initial position X1 and when the contoured plates 52, 54 are positioned apart at position X2 respectively. The first fixed contoured plate 52, which incorporates a cylinder 58, is mounted directly on the stand 50. The second movable contoured plate 54 incorporates a piston 56 that is moved into and out of the cylinder 58 and is free to move with respect to the first fixed contoured plate 52. The actuating means 58, 56 may comprise a pneumatic or hydraulic cylinder or piston, as in the illustrated embodiment, or any other means for moving the two contoured plates 52, 54 together and apart. One or more support rods for supporting the second contoured plate 54 may be provided between the contoured plates 52, 54 to support the second contoured plate 54 as it moves.

Figure 9:
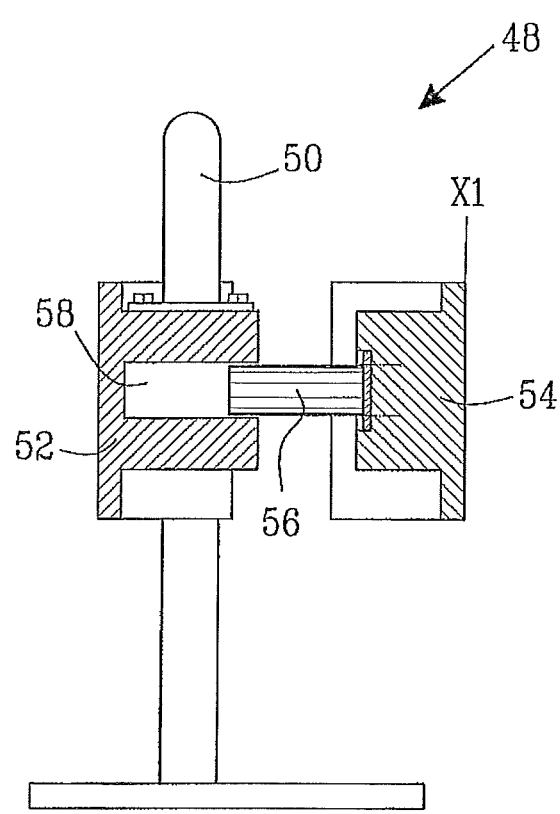
Figure 10:
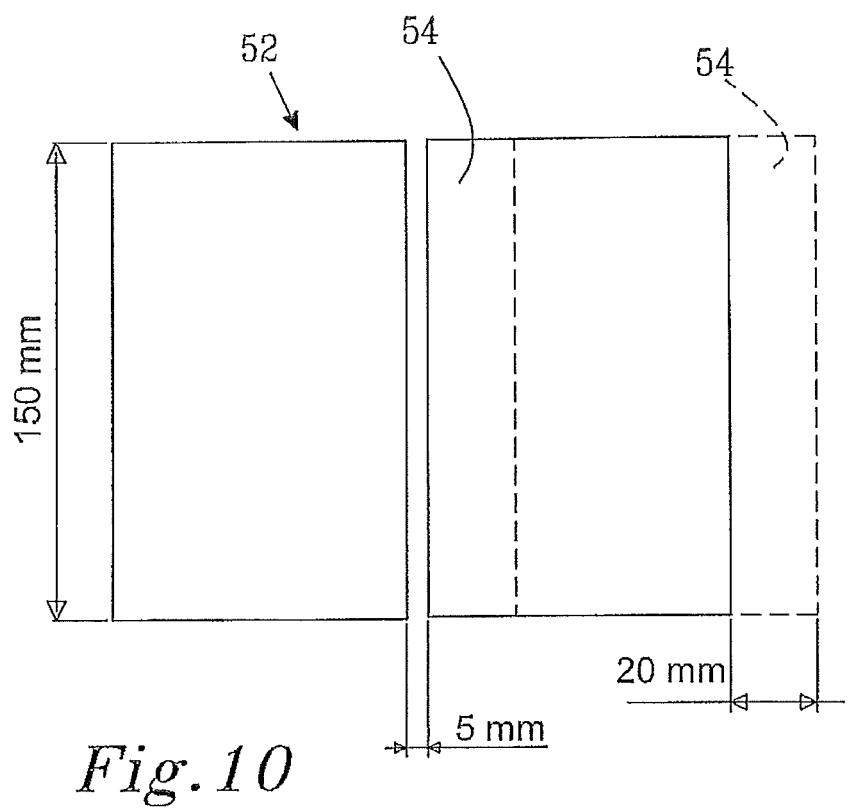
Figure 11:
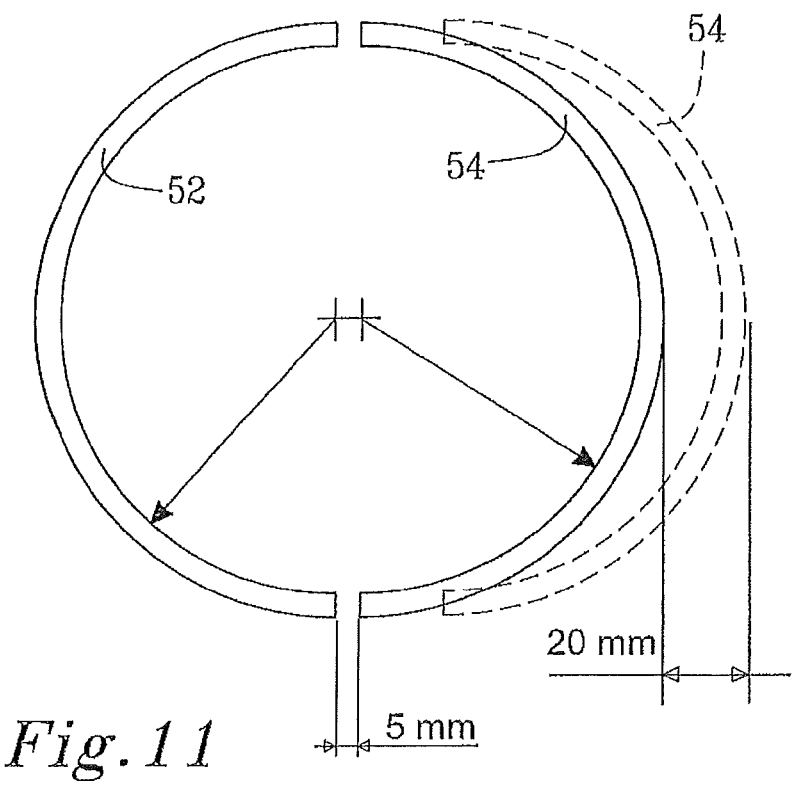

FIGS. 9 and 10 schematically show the two contoured plates 52, 54, of the Cyclic Waist Expansion Test Apparatus 48 from the side and from above respectively. The first and second contoured plates 52, 54 have a substantially semi-circular cross-section and are constituted of half circles of outer radius 80.2 mm, resulting in a circumference of 504 mm when the contoured plates 52, 54 are located adjacently to one another. The two contoured plates are assembled with the open ends of their respective semi-circular-shaped cross sections facing one another so as to form a substantially circular shape resembling the shape of a human waist, especially a baby's waist. The second contoured plate 54 is moved through a predetermined distance from an inner position X1 to an outer position X2 mechanically. This predetermined distance is 10 mm when carrying out the Cyclic Waist Expansion Test, giving a circumference change of 20 mm.

Both contoured plates 52, 54 have a height of 150 mm, comprise austenitic stainless steel (DIN 1.4301, SIS 2333, AISI 304) having a grain size of 0.3 µm and their surface is covered with a polyethyulene terepthalate material, namely Scrynel Petex® PET59HC which is available from Sefar AG, Mesh & Technology, 8803 Rüschlikon, Switzerland under Sefar AG product reference number 07-59/33 which has a mesh opening of 59 µm, an open area of 33%, a mesh count, warp of 97 n/cm, a mesh count, weft of 97 n/cm, a yarn diameter, warp of 44 µm, a yarn diameter, weft of 44 µm, a weight of 35 g/m² and a thickness of 65 µm. This material is adhered to the contoured plates using double-sided adhesive. One side of the material is coated with adhesive over its entire surface apart from a 2-3 mm wide zone along its edges (in order to eliminate the risk of adhesive coating the side of the material that will constitute the outer surface of the Cyclic Waist Expansion Test apparatus to which absorbent articles will be fastened) and the material is then stuck onto the contoured plates.

When the contoured plates 52, 54 are in their inner position X1 there is a distance of 5 mm between them. Such a distance is necessary to ensure that absorbent articles are not clamped between the contoured plates. If the shortest distance between the two contoured plates were 0 mm, there would be a risk of the absorbent articles getting stuck in the nip between the two contoured plates instead of falling therefrom once their elastic regions had been permanently deformed.

The Cyclic Waist Expansion Test comprises the steps of:

Ensuring that the second contoured plate 54 is set at its inner position X1.

Unfolding the absorbent article 10 and positioning the upper edge 12c of a front panel 16 parallel to the upper edge of the first contoured plate 52 and 32 mm therefrom, whereby the vertical position of the upper edge 12c may be marked on the first contoured plate.

Figure 12:
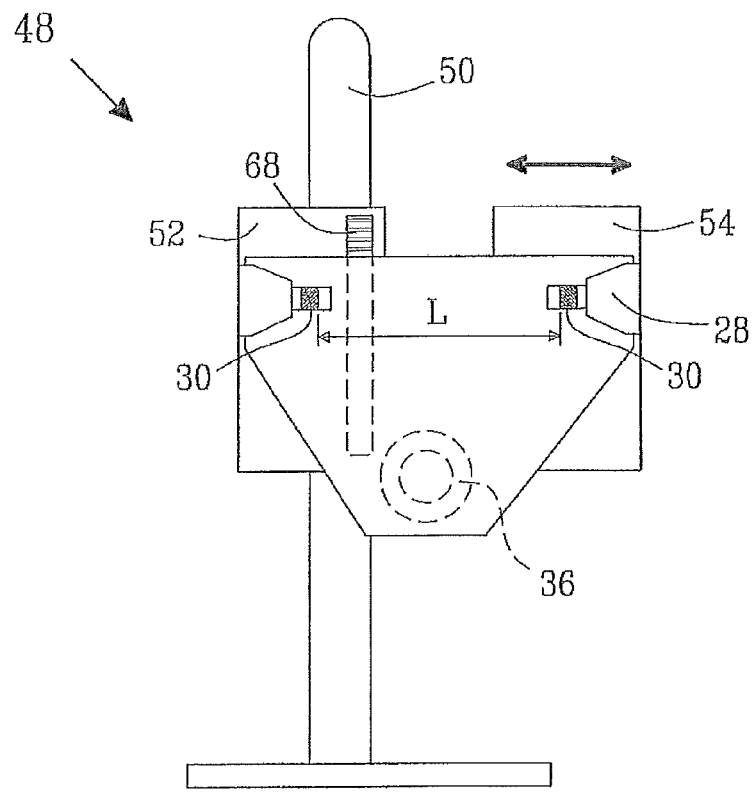

Wrapping the hanging crotch portion of the absorbent article 10 under the contoured plates 52, 54 and fastening the front panel 16 to the back panel 20 so that the middle of the transverse edge 12d of the front panel 16 of the absorbent article 10 is located in between the contoured plates 52,54 of the Cyclic Waist Expansion Test apparatus. The front and back panels may be temporarily held in place on the contoured plates using clamps. It is important to ensure that the elastic regions are elongated by the amount that they would be if subjected to a force of 7N on the tensile testing apparatus and that the elastic regions of all of the absorbent articles being tested are stretched by the same amount. This is done by determining the length $L_{7N}$, of each absorbent article, using the method described above in conjunction with FIG. 5, and then fastening the absorbent article 10 around the contoured plates 52, 54 so that is has a circumference equal to the tensioning distance. The tensioning distance, L, which is measured between the innermost edges of the first fastening means 30 when attached to the complementary second fastening means 32 (as indicated in FIG. 12), may be calculated using the equation;

$$L=C-L_{7N}$$

where C is the circumference of the contoured plates, namely 504 mm and $L_{7N}$ is the length of the of the rear waist region 22 of that absorbent article 22 when subjected to a force of 7N on the tensile testing apparatus described herein.

Figure 13:
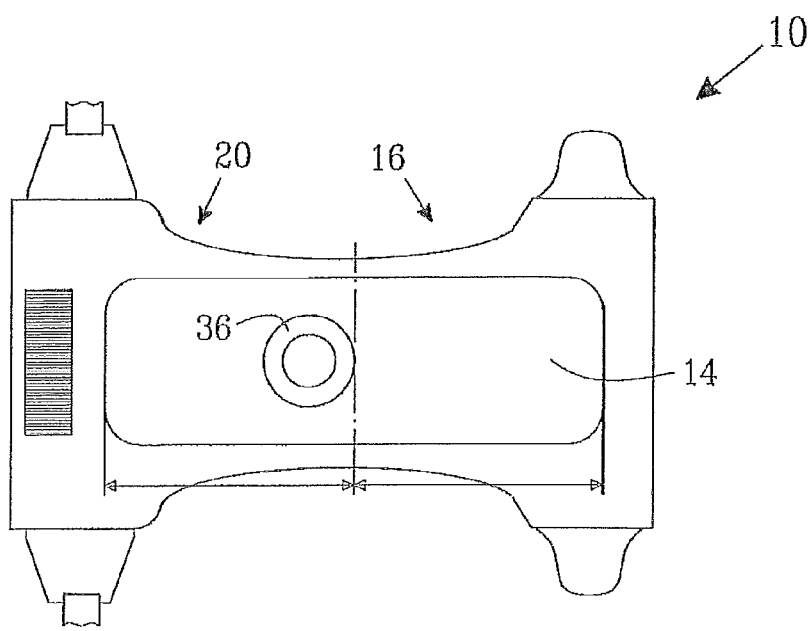
FIG. 13 shows the position in which a weight is placed in an absorbent article during the Cyclic Waist Expansion Test Apparatus, and FIG. 14 schematically shows the stripe light projection (SLP) apparatus used to measure the surface roughness of a front side panel of an absorbent article.
Figure 14:
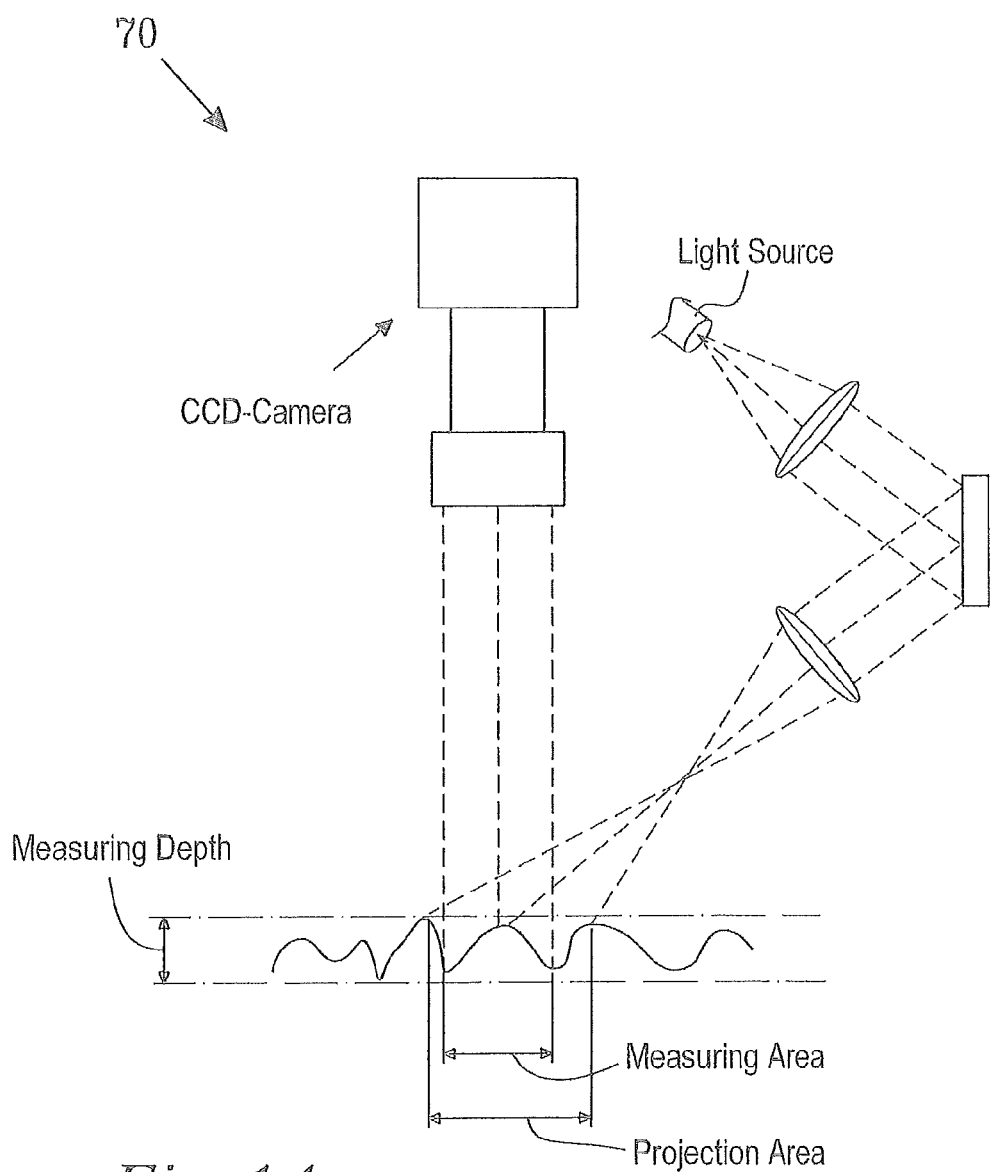

Putting a weight 100 g (namely a brass ring having an outer diameter of 47 mm, and inner diameter of 35 mm and a height of 13 mm) inside the crotch portion of the absorbent article. The weight is placed just forward of the centre of the absorbent structure of the absorbent article in the front panel of the absorbent article (as shown in FIG. 13). If clamps have been used, these are then removed.

Starting the pneumatic cylinder and letting the two contoured plates 52, 54 move through fifteen expansion and contraction cycles. When the last cycle is complete the two contoured plates 52, 54 are arranged to stop at the inner position X1 at a distance 5 mm apart.

Marking or noting the position of the top edge 12c/12a of the absorbent article thirty seconds after the fifteenth expansion and contraction cycle had been completed and measuring/calculating the vertical distance between the first and second marks or positions, thus providing the distance through which absorbent article has slipped if the absorbent article still remains on the Cyclic Waist Expansion Test.

In order to pass the Cyclic Waist Expansion Test fifteen absorbent articles of the same size and type must be tested and the average distance which the fifteen absorbent articles may slip down may be no more than 15 mm from their initial position on the Cyclic Waist Expansion Test during fifteen expansion/contraction cycles. The measurement of the distance each absorbent article had slipped was made within 5-10 seconds after the completion of the fifteen expansion/contraction cycles. The measurement is taken at the middle of the transverse edge 12d of the front panel 16 of the absorbent article. An absorbent article or its packaging may then be marked with information and/or a parameter that is indicative of how well the absorbent article stays in place on a user's waist when in use.

FIG. 12 shows an absorbent article 10 fastened around the test equipment. The test equipment may comprise a vertical scale 68 so that the initial position of an edge of a waist region 18, 22 of the absorbent article 10 may be recorded as well as its position after each, or all of the expansion and contraction cycles. The actuating means may then move the contoured plates 52, 54 through fifteen expansion and contraction cycles for example (where one such cycle involves moving the movable contoured plate 54 from X1 to X2 and back to X1 again). The tensioning distance, L, has been indication in FIG. 12.

Fifteen samples of each of eight different commercially available absorbent articles (of different types and sizes) were tested under the same conditions using the Cyclic Waist Expansion Test. Fifteen samples of the absorbent article according to the present invention were also tested and compared to the commercially available products. The tests were carried out in a climatised room at a temperature of 23±1° C., relative humidity of 50±5% whereby the samples to be tested were climatised in the room for at least two hours before the tests.

The following tables show the vertical distance of each tested absorbent article and the average vertical distance of each set of fifteen tested absorbent articles.

The symbol "√" indicates that the product passed the test, i.e. the average distance of the fifteen tested absorbent articles was no more than 15 mm from their initial position on the Cyclic Waist Expansion Test apparatus during fifteen expansion/contraction cycles and within 5-10 seconds after the completion of fifteen expansion and contraction cycles.

The symbol "X" indicates that the product failed the test, i.e. the average distance of the fifteen tested absorbent articles was more than 15 mm from their initial position on the Cyclic Waist Expansion Test apparatus during fifteen expansion and contraction cycles or within 5-10 seconds after the completion of fifteen expansion and contraction cycles.

| Inventive product manufactured by SCA | | | | | |
|---|---|---|---|---|---|
| Product code 61205M1 264746 Tensioning distance L = 135 mm Size 3 | | Product code 060929 FG092059 Tensioning distance L = 96 mm Size 4 | | Product code 130407 FG090659 Tensioning distance L = 45 mm Size 5 | |
| Sample | Vertical distance (mm) | Sample | Vertical distance (mm) | Sample | Vertical distance (mm) |
| 1 | 13 | 1 | 18 | 1 | 8 |
| 2 | 12 | 2 | 11 | 2 | 7 |
| 3 | 14 | 3 | 16 | 3 | 8 |
| 4 | 12 | 4 | 8 | 4 | 7 |
| 5 | 12 | 5 | 12 | 5 | 7 |
| 6 | 18 | 6 | 10 | 6 | 10 |
| 7 | 15 | 7 | 16 | 7 | 7 |
| 8 | 13 | 8 | 15 | 8 | 6 |
| 9 | 13 | 9 | 10 | 9 | 7 |
| 10 | 16 | 10 | 13 | 10 | 8 |
| 11 | 16 | 11 | 11 | 11 | 7 |
| 12 | 14 | 12 | 12 | 12 | 7 |
| 13 | 14 | 13 | 13 | 13 | 8 |
| 14 | 14 | 14 | 10 | 14 | 9 |
| 15 | 15 | 15 | 13 | 15 | 7 |
| mean | 14.1 | mean | 12.5 | mean | 7.5 |
| | √ | | √ | | √ |

| Active Fit manufactured by Procter & Gamble | | | | | |
|---|---|---|---|---|---|
| Product code 08022007 7 039 4499 74 05:52 E Tensioning distance L = 134 mm Size 3 | | Product code 21092006 6 264 4499 75 06:22 E Tensioning distance L = 111 mm Size 4 | | Product code 13102006 6 286 4499 76 21:10 E Tensioning distance L = 97 mm Size 5 | |
| Sample | Vertical distance (mm) | Sample | Vertical distance (mm) | Sample | Vertical distance (mm) |
| 1 | 21 | 1 | 19 | 1 | 11 |
| 2 | 23 | 2 | 17 | 2 | 11 |
| 3 | 20 | 3 | 17 | 3 | 9 |
| 4 | 18 | 4 | 16 | 4 | 9 |
| 5 | 23 | 5 | 18 | 5 | 10 |
| 6 | 22 | 6 | 19 | 6 | 18 |
| 7 | 22 | 7 | 14 | 7 | 13 |
| 8 | 23 | 8 | 17 | 8 | 13 |
| 9 | 23 | 9 | 18 | 9 | 13 |
| 10 | 18 | 10 | 17 | 10 | 13 |
| 11 | 18 | 11 | 14 | 11 | 23 |
| 12 | 17 | 12 | 19 | 12 | 14 |
| 13 | 19 | 13 | 17 | 13 | 16 |
| 14 | 20 | 14 | 17 | 14 | 14 |
| 15 | 20 | 15 | 16 | 15 | 12 |
| mean | 20.5 | mean | 17.0 | mean | 13.3 |
| | X | | X | | √ |

| Huggies Super Flex manufactured by Kimberly Clark ||||||
|---|---|---|---|---|---|
| Product code BO6186111831 1 FAB: 050706 VAL: 050709 Tensioning distance L = 147 mm Size 3 || Product code BO07361223221 FAB: 05/02/07 VAL: 05/0210 Tensioning distance L = 143 mm Size 4 || Product code B07030060047 1 FAB: 300107 VAL: 300110 Tensioning distance L = 105 mm Size 5 ||
| Sample | Vertical distance (mm) | Sample | Vertical distance (mm) | Sample | Vertical distance (mm) |
| 1 | 15 | 1 | 15 | 1 | 8 |
| 2 | 13 | 2 | 13 | 2 | 8 |
| 3 | 13 | 3 | 12 | 3 | 7 |
| 4 | 15 | 4 | 13 | 4 | 5 |
| 5 | 14 | 5 | 15 | 5 | 6 |
| 6 | 12 | 6 | 11 | 6 | 6 |
| 7 | 13 | 7 | 12 | 7 | 6 |
| 8 | 12 | 8 | 11 | 8 | 5 |
| 9 | 16 | 9 | 13 | 9 | 7 |
| 10 | 14 | 10 | 10 | 10 | 4 |
| 11 | 12 | 11 | 10 | 11 | 9 |
| 12 | 17 | 12 | 11 | 12 | 7 |
| 13 | 14 | 13 | 10 | 13 | 10 |
| 14 | 13 | 14 | 11 | 14 | 7 |
| 15 | 14 | 15 | 10 | 15 | 9 |
| mean | 13.8 | mean | 11.8 | mean | 6.9 |
| | ✓ | | ✓ | | ✓ |

| Huggies Natural Fit manufactured by Kimberly Clark ||||||
|---|---|---|---|---|---|
| Product code B06353080524 1 FAB 9/12/06 VAL: 19/12/09 Tensioning distance L = 155 mm Size 3 || Product code B07055080940 1 FAB24*/02/07 VAL24/02/10 Tensioning distance L = 123 mm Size 4 || Product code BO6339080549 1 FAB: 05/12/06 VAL 05/12/09 Tensioning distance L = 107 mm Size 5 ||
| Sample | Vertical distance (mm) | Sample | Vertical distance (mm) | Sample | Vertical distance (mm) |
| 1 | 17 | 1 | 9 | 1 | 6 |
| 2 | 18 | 2 | 9 | 2 | 7 |
| 3 | 14 | 3 | 9 | 3 | 7 |
| 4 | 15 | 4 | 9 | 4 | 6 |
| 5 | 14 | 5 | 8 | 5 | 6 |
| 6 | 14 | 6 | 9 | 6 | 8 |
| 7 | 13 | 7 | 9 | 7 | 5 |
| 8 | 16 | 8 | 9 | 8 | 9 |
| 9 | 16 | 9 | 9 | 9 | 8 |
| 10 | 16 | 10 | 9 | 10 | 6 |
| 11 | 16 | 11 | 8 | 11 | 7 |
| 12 | 15 | 12 | 9 | 12 | 8 |
| 13 | 17 | 13 | 8 | 13 | 6 |
| 14 | 14 | 14 | 10 | 14 | 6 |
| 15 | 15 | 15 | 10 | 15 | 7 |
| mean | 15.3 | mean | 8.9 | mean | 6.8 |
| | X | | ✓ | | ✓ |

| George manufactured by ASDA ||||||||
|---|---|---|---|---|---|---|---|
| Product code 6355A2020738 MIDI Tensioning distance L = 100 mm Size 3 || Product code 7045A2021945 MAXI Tensioning distance L = 63 mm Size 4 || Product code 7068A2021615 MAXI PLUS Tensioning distance L = 67 mm Size 4+ || Product code 7062A2020211 JUNIOR Tensioning distance L = 66 mm Size 5 ||
| Sample | Vertical distance (mm) | Sample | Vertical distance (mm) | Sample | Vertical distance (mm) | Sample | Vertical distance (mm) |
| 1 | 15 | 1 | 11 | 1 | 14 | 1 | 14 |
| 2 | 12 | 2 | 11 | 2 | 12 | 2 | 11 |
| 3 | 15 | 3 | 10 | 3 | 13 | 3 | 12 |

-continued

| George manufactured by ASDA ||||||||
| Product code 6355A2020738 MIDI Tensioning distance L = 100 mm Size 3 || Product code 7045A2021945 MAXI Tensioning distance L = 63 mm Size 4 || Product code 7068A2021615 MAXI PLUS Tensioning distance L = 67 mm Size 4+ || Product code 7062A2020211 JUNIOR Tensioning distance L = 66 mm Size 5 ||
| Sample | Vertical distance (mm) | Sample | Vertical distance (mm) | Sample | Vertical distance (mm) | Sample | Vertical distance (mm) |
|---|---|---|---|---|---|---|---|
| 4 | 18 | 4 | 10 | 4 | 15 | 4 | 12 |
| 5 | 18 | 5 | 11 | 5 | 14 | 5 | 13 |
| 6 | 17 | 6 | 14 | 6 | 15 | 6 | 11 |
| 7 | 18 | 7 | 12 | 7 | 15 | 7 | 12 |
| 8 | 20 | 8 | 12 | 8 | 11 | 8 | 9 |
| 9 | 19 | 9 | 13 | 9 | 16 | 9 | 11 |
| 10 | 20 | 10 | 15 | 10 | 13 | 10 | 11 |
| 11 | 18 | 11 | 12 | 11 | 14 | 11 | 10 |
| 12 | 17 | 12 | 12 | 12 | 12 | 12 | 10 |
| 13 | 17 | 13 | 10 | 13 | 13 | 13 | 12 |
| 14 | 12 | 14 | 14 | 14 | 14 | 14 | 13 |
| 15 | 16 | 15 | 15 | 15 | 13 | 15 | 12 |
|  | 16.8 |  | 12.1 | mean | 13.6 | mean | 11.5 |
|  | X |  | ✓ |  | ✓ |  | ✓ |

| Boots manufactured by Boots ||||||
| Prd kod 709061608 Tensioning distance L = 68 mm Weight 100 g Size 4 || 1 909 062 008 Tensioning distance L = 67 mm Weight 100 g Size 4+ || 1 801 072 015 Tensioning distance L = 66 mm Weight 100 g Size 5 ||
| Sample | Vertical distance (mm) | Sample | Vertical distance (mm) | Sample | Vertical distance (mm) |
|---|---|---|---|---|---|
| 1 | 16 | 1 | 10 | 1 | 14 |
| 2 | 15 | 2 | 12 | 2 | 12 |
| 3 | 17 | 3 | 13 | 3 | 14 |
| 4 | 16 | 4 | 14 | 4 | 11 |
| 5 | 15 | 5 | 15 | 5 | 14 |
| 6 | 16 | 6 | 18 | 6 | 14 |
| 7 | 15 | 7 | 13 | 7 | 13 |
| 8 | 14 | 8 | 12 | 8 | 13 |
| 9 | 14 | 9 | 10 | 9 | 12 |
| 10 | 15 | 10 | 12 | 10 | 14 |
| 11 | 17 | 11 | 15 | 11 | 14 |
| 12 | 16 | 12 | 16 | 12 | 13 |
| 13 | 12 | 13 | 19 | 13 | 10 |
| 14 | 18 | 14 | 15 | 14 | 16 |
| 15 | 16 | 15 | 13 | 15 | 18 |
| mean | 15.5 | mean | 13.8 | mean | 13.5 |
|  | X |  | ✓ |  | ✓ |

| Carrefour manufactured by Carrefour ||||||||
| Sample | Vertical distance (mm) | Sample | Vertical distance (mm) | Sample | Vertical distance (mm) | Sample | Vertical distance (mm) |
|---|---|---|---|---|---|---|---|
| 1 | 18 | 1 | 15 | 1 | 12 | 1 | 14 |
| 2 | 17 | 2 | 7 | 2 | 14 | 2 | 12 |
| 3 | 17 | 3 | 10 | 3 | 14 | 3 | 12 |
| 4 | 13 | 4 | 12 | 4 | 12 | 4 | 14 |
| 5 | 18 | 5 | 11 | 5 | 13 | 5 | 13 |
| 6 | 15 | 6 | 9 | 6 | 14 | 6 | 16 |
| 7 | 17 | 7 | 9 | 7 | 15 | 7 | 15 |
| 8 | 18 | 8 | 13 | 8 | 12 | 8 | 13 |
| 9 | 17 | 9 | 15 | 9 | 12 | 9 | 13 |

-continued

| Carrefour manufactured by Carrefour | | | | | | | |
|---|---|---|---|---|---|---|---|
| Sample | Vertical distance (mm) | Sample | Vertical distance (mm) | Sample | Vertical distance (mm) | Sample | Vertical distance (mm) |
| 10 | 17 | 10 | 15 | 10 | 13 | 10 | 12 |
| 11 | 16 | 11 | 9 | 11 | 14 | 11 | 10 |
| 12 | 16 | 12 | 11 | 12 | 12 | 12 | 13 |
| 13 | 18 | 13 | 11 | 13 | 12 | 13 | 14 |
| 14 | 19 | 14 | 9 | 14 | 14 | 14 | 13 |
| 15 | 17 | 15 | 11 | 15 | 12 | 15 | 13 |
| mean | 16.9 | mean | 11.1 | mean | 13.0 | mean | 13.1 |
|  | X |  | ✓ |  | ✓ |  | ✓ |

| Monneyman manufactured by Unicharm | | | |
|---|---|---|---|
| Prdkod 852216082 (M) Tensioning distance L = 155 mm Size M | | Prd kod 852037093 (L) Tensioning distance L = 134 mm Size L | |
| Sample | Vertical distance (mm) | Sample | Vertical distance (mm) |
| 1 | 20 | 1 | 19 |
| 2 | 20 | 2 | 17 |
| 3 | 20 | 3 | 17 |
| 4 | 20 | 4 | 16 |
| 5 | 18 | 5 | 19 |
| 6 | 21 | 6 | 16 |
| 7 | 21 | 7 | 17 |
| 8 | 18 | 8 | 17 |
| 9 | 20 | 9 | 17 |
| 10 | 19 | 10 | 18 |
| 11 | 21 | 11 | 17 |
| 12 | 18 | 12 | 17 |
| 13 | 20 | 13 | 19 |
| 14 | 18 | 14 | 17 |
| 15 | 19 | 15 | 18 |
| mean | 19.5 | mean | 17.4 |
|  | X |  | X |

Even though several of the tested products did not slip down more than 15 mm on the Cyclic Waist Expansion Test Apparatus within 5-10 seconds after the completion of fifteen expansion and contraction cycles, none of the tested products exhibited the same structural features as the inventive product, namely the elastic regions of the tested products were not tailored in the same way as the elastic regions of the inventive product.

Further modifications of the invention within the scope of the claims would be apparent to a skilled person.

The invention claimed is:

1. An absorbent article comprising
a chassis extending about a longitudinal axis, said chassis including a topsheet, a backsheet and an absorbent structure disposed between said topsheet and said backsheet, said chassis having a first transverse axis dividing the absorbent structure into a front body panel terminating in a front waist region and a rear body panel terminating in a rear waist region, a pair of opposed front side panels attached to said front body panel, said rear waist region having a first elastic, said chassis being delimited by opposed longitudinal edges and opposed front and back transverse edges;
a pair of opposed rear side panels attached to said chassis at said rear waist region of said rear body panel, each rear side panel extending outwardly from the respective longitudinal edge of the chassis, at least one of said rear side panels having a second elastic, and
a fastening system for fastening the absorbent article around the waist of a user, the fastening system comprising a first fastener arranged on said pair of opposed rear side panels and a complementary second fastener arranged on said front body panel,
wherein in said rear waist region,
said absorbent structure terminates at a first distance from said back transverse edge and
said first elastic extends substantially parallel to said back transverse edge and spaced therefrom by a second distance and spaced from said absorbent structure by a third distance, said first elastic terminating short of a first longitudinal edge by a fourth distance, wherein said third distance is greater than said second distance or substantially equal thereto;
said fastening system comprises the first fastener on each opposed rear side panel, said first fasteners being positioned on a second transverse axis extending substantially parallel to said first transverse axis, with said second transverse axis being a transverse centerline of the first fasteners passing between said absorbent structure and said first elastic;
wherein the front side panels have a surface roughness where a height between 5% of a surface of the material constituting the front side panel and 95% of the surface of the material constituting the front side panel is 46 to 48 μm; and wherein
said first distance is between 40-140 mm;
said second distance is between 5-40 mm;
said third distance is between 10-60 mm;
said fourth distance is between 30-120 mm;
the ratio of said second distance to said first distance is between 1:2 and 1:9; and
the ratio of said third distance to said first distance is between 1:3 and 1:9.

2. An absorbent article according to claim 1, wherein said first and second elastics are tailored such that when tested on a Cyclic Waist Expansion Test apparatus, the absorbent article does not slip down more than 15 mm from its initial position on the Cyclic Waist Expansion Test apparatus during at least fifteen expansion/contraction cycles of the Cyclic Waist Expansion Test and within 5-10seconds after being subjected to at least fifteen expansion/contraction cycles of the Cyclic Waist Expansion Test.

3. An absorbent article according to claim 1, wherein said first and second elastics are tailored such that when tested on a tensile testing apparatus using a force of 7N, the ratio of the extension of the first elastic to the extension of the second elastic is in the range 35:60 to 50:60.

4. An absorbent article according to claim 1, wherein said first elastic terminates short of each opposed longitudinal edge by said fourth distance.

5. An absorbent article according to claim 1, wherein said first elastic is constituted by an elastic film.

6. An absorbent article according to claim 1, wherein said second elastic constitutes an elastic laminate comprising at least one elastic film layer and at least one non-woven layer, in which the layers have been ultrasonically bonded, adhesively bonded or extrusion bonded, or bonded using a combination of said bonding methods.

7. An absorbent article according to claim 1, wherein said second elastic constitutes an elastic laminate comprising at least one elastic film layer and at least one non-woven layer, in which the layers have been ultrasonically bonded, whereby projections on the side of the area in which the layers have been bonded are arranged to be located towards the body of a user of the absorbent article when said absorbent article is in use.

8. An absorbent article according to claim 1, wherein said second elastic is constituted by substantially the entire said at least one rear side panel.

9. An absorbent article according to claim 1, wherein the ratio of said fourth distance to the width of the rear body panel in the rear waist region is between 1:20 to 1:45.

10. An absorbent article according to claim 1, wherein said first elastic extends along 25-55% of the width of the rear body panel in the rear waist region in the transverse direction of the absorbent article.

11. An absorbent article according to claim 1, wherein said first elastic extends 1 to 5 cm in the longitudinal direction of the absorbent article.

12. An absorbent article according to claim 1, wherein said absorbent structure in the rear body panel is thinner than said absorbent structure in the front body panel.

13. An absorbent article according to claim 1, wherein said absorbent structure is thinnest in the vicinity of the rear waist region.

14. An absorbent article according to claim 1, comprising a material constituting at least one breathable zone, which is located in between a longitudinal edge of the chassis and a longitudinally extending edge of the first elastic.

15. An absorbent article according to claim 1, wherein said first elastic is located between said topsheet and said backsheet.

16. An absorbent article according to claim 1, wherein each of said opposed longitudinal edges comprises a leg contour and said absorbent article comprises leg elastic that is arranged to extend in a curved line that is substantially parallel to said leg contour when said chassis is fully extended.

17. An absorbent article according to claim 1, wherein said chassis comprises at least one absorbent-structure-free channel that extends substantially in the longitudinal direction of the absorbent article.

18. An absorbent article according to claim 1, wherein the absorbent article is one for a child.

19. An absorbent article according to claim 18, wherein the absorbent article is one for a child that weighs 4-25 kg.

20. An absorbent article according to claim 1, wherein the absorbent article is arranged to be fastenable around the contoured plates of the Cyclic Waist Expansion Test apparatus.

21. An absorbent article according to claim 1, wherein the absorbent article comprises elastics in the rear waist region and no elastics in the front waist region.

22. An absorbent article according to claim 1, wherein material of the second elastic is uniform along the second transvers axis.

23. An absorbent article according to claim 1, wherein the front side panels are formed of a non-woven material.

* * * * *